US011309068B2

(12) United States Patent
Hanz et al.

(10) Patent No.: US 11,309,068 B2
(45) Date of Patent: Apr. 19, 2022

(54) ELECTRONIC PRESCRIPTION DELIVERY SYSTEM AND METHOD

(71) Applicant: NEXTGEN MANAGEMENT LLC, Boca Raton, FL (US)

(72) Inventors: Ezra Hanz, Boca Raton, FL (US); Jeffrey Arthur Stahl, Boca Raton, FL (US); Lewis Arnold Stahl, Boca Raton, FL (US)

(73) Assignee: NEXTGEN MANAGEMENT LLC, Boca Raton, GA (US)

( * ) Notice: Subject to any disclaimer, the term of this patent is extended or adjusted under 35 U.S.C. 154(b) by 0 days.

(21) Appl. No.: 17/357,205

(22) Filed: Jun. 24, 2021

(65) Prior Publication Data

US 2021/0319871 A1 Oct. 14, 2021

Related U.S. Application Data

(63) Continuation of application No. 13/198,103, filed on Aug. 4, 2011, now Pat. No. 11,049,597.

(Continued)

(51) Int. Cl.
*G16H 10/60* (2018.01)
*G16H 20/10* (2018.01)

(52) U.S. Cl.
CPC .............. *G16H 20/10* (2018.01); *G16H 10/60* (2018.01)

(58) Field of Classification Search
CPC ................................ G16H 20/10; G16H 10/60
(Continued)

(56) References Cited

U.S. PATENT DOCUMENTS

2002/0042726 A1  4/2002  Mayaud
2002/0138303 A1  9/2002  Enos
(Continued)

FOREIGN PATENT DOCUMENTS

WO    0135376    5/2001
WO    03077183   9/2003
(Continued)

OTHER PUBLICATIONS

Yendluri, Sravanthi; Mobile Prescription; University of Nevada, Reno. ProQuest Dissertations Publishing, 2008 (Year: 2008).*

(Continued)

*Primary Examiner* — Hiep V Nguyen
(74) *Attorney, Agent, or Firm* — FisherBroyles LLP (57) ABSTRACT

The invention is a computer-implemented method and apparatus that delivers information to a prescriber that is prescribing medication via an electronic prescription system, the information is delivered at the time of entering the prescription and prior to completion of entering the prescription information. The information delivered is responsive to information about the prescriber, the patient, and/or other relevant conditions from any or all of a number of sources. The information delivered to the prescriber may include drug interaction information, warnings, legally required statements, potential alternative medications, advertisements, coupons, etc. The data to which the specific information delivered to the prescriber is responsive may include prescriber information, such as the location, age, gender, medical specialty, practice size, geographic location etc, information about the patient, such as age, gender, insurance information, location, previous medical history, height, weight, etc. The data also may include information not specific to the prescriber or patient per se, such as local or national laws, current local weather, local allergen counts, (Continued)

etc. The data may be collected from various sources, including the prescriber's medical records database, insurance carrier databases, public information available over the internet or from other sources, purchased information such as subscription lists, weather, pollution, and allergy information, etc.

22 Claims, 3 Drawing Sheets

Related U.S. Application Data (60) Provisional application No. 61/370,632, filed on Aug. 4, 2010.

(58) Field of Classification Search
USPC .............................................................. 705/3
See application file for complete search history.

(56) References Cited

U.S. PATENT DOCUMENTS

| | | |
|---|---|---|
| 2003/0050799 A1 | 3/2003 | Jay |
| 2003/0187692 A1 | 10/2003 | Park |
| 2003/0233252 A1* | 12/2003 | Haskell ................. G06Q 10/10 705/2 |
| 2005/0010435 A1 | 1/2005 | Kato |
| 2007/0203749 A1 | 8/2007 | Chunduru |
| 2008/0021739 A1 | 1/2008 | Brock |
| 2008/0208986 A1 | 8/2008 | Kobylevsky |
| 2008/0222042 A1* | 9/2008 | Moore ................... G16H 20/10 705/55 |
| 2010/0038273 A1 | 2/2010 | Johnson |

FOREIGN PATENT DOCUMENTS

| | | | |
|---|---|---|---|
| WO | 2004051428 | 6/2004 | |
| WO | WO-2009006641 A1 * | 1/2009 | ............. G16H 10/60 |

OTHER PUBLICATIONS

International Search Report issued in PCT/US2011/046592, dated Nov. 20, 2011 along with Written Opinion.

* cited by examiner

ELECTRONIC PRESCRIPTION DELIVERY SYSTEM AND METHOD

RELATED APPLICATION

This application is a continuation of U.S. application Ser. No. 13/198,103, filed Aug. 4, 2011, which claims priority to U.S. Provisional Patent Application No. 61/370,632 filed Aug. 4, 2010, which are incorporated herein fully by reference.

FIELD

The invention disclosed herein relates generally to a method and system for providing electronic messaging, including advertising and promotional messages and educational or informational messages about a given drug, such as newly-discovered indications, contraindications, drug-drug interactions, and/or drug-food interactions on an electronic prescription interface to a health care professional or patient.

BACKGROUND

Prescriptions are oral, written, or electronic submissions of medical orders that include the name, address and other identifying information of a patient; the name, dosage, and directions for use of a drug; the date of issue; and are signed by the prescriber, who is a qualified medical practitioner.

Physicians write approximately 2.5 billion prescriptions each year. Adverse drug events are known to decline when physicians electronically prescribe medication because physician handwriting may be illegible to pharmacists. Moreover, the writing of prescriptions by unauthorized persons continues to be a problem because the current systems are easily duplicated. These shortcomings have contributed to rising health care and drug prescription costs. These challenges have led to an increased use of electronic medical records (EMR) for the management of patient files and increased use of electronic prescription systems.

Prior to the advent of EMR systems, prescriptions for individual patient medical needs were handwritten by physicians or other qualified health care professionals on pre-printed prescription pads. The pages of a pre-printed prescription pad typically includes text that identifies the document as a prescription, the name and address of the prescribing provider, and any legally require data, such as a Drug Enforcement Agency (DEA) registration number, and a signature of the provider. The physician hands the prescription to the patient and the patient delivers the prescription to a pharmacist who will administer the drug as per the specifications on the prescription.

Prescription pads are used by the pharmaceutical industry for direct-to-physician advertisement to increase brand awareness and improve brand recall. For instance, it is common for a paper pre-printed prescription pads to have an advertisement for a pharmaceutical company or drug listed on every fifth page.

Electronic prescription dispensing systems typically include the steps of entering patient information electronically into an electronic medical record (EMR) system, such as disclosed by U.S. Published Patent Application No. 2003/0187692, herein incorporated by reference in its entirety. The prescriber enters the patient information and necessary prescription information, such as drug and dosage, into the EMR system via a suitable graphic user interface (GUI) as known in the art.

Pharmaceutical companies and others are now also able to message medical providers via the electronic interfaces of electronic medical systems.

SUMMARY

The invention is a computer-implemented method and apparatus that delivers information to a physician that is prescribing medication via an electronic prescription system. The information is delivered while the prescriber is entering the prescription and prior to completion of the prescription. The information delivered to the prescriber is responsive to information about the prescriber, the patient, and/or other relevant conditions from any or all of a number of sources. The information delivered to the prescriber may include drug interaction information, warnings, legally required statements, potential alternative medications, advertisements, patient-directed coupons, etc. The data to which the specific information delivered to the prescriber is responsive may include prescriber information, such as the location, age, gender, past prescribing habits, medical specialty, practice size, geographic location (e.g., by zip code), socio-economic data about the geographic location of the prescriber's practice, decile, schooling, years in practice, etc. Information about the patient may include, for instance, age, gender, height, weight, ethnicity, family medical history, allergies, pre-existing medical conditions, patient prescription history, insurance information (e.g., co-pay amount), educational level, home location, previous medical history, socio-economic data, etc. The data also may include information not specific to the prescriber or patient per se, such as local or national laws, current local weather, local pollen counts and other allergen data, etc.

The data may be collected from various sources, including the prescribing physician's own medical records database (e.g., the database of the prescriber's practice management software system), the databases of other physicians treating the same patient, insurance carrier databases, public information available over the internet or from other sources, purchased information such as subscription lists, weather, pollution, and daily allergen information, etc.

DETAILED DESCRIPTION OF PREFERRED EMBODIMENTS

Eprescribing is known. At its simplest, eprescribing is a system for allowing prescribers to write prescriptions for medications for patients electronically, e.g., by entering the necessary data into an electronic apparatus, such as a computer, smart phone, or other handheld electronic device, and have the prescription sent electronically to the prescription filler, e.g., a pharmacy. Hence, an eprescription system typically comprises a software application running on the prescriber's computer, smart phone or other device, a software application running at a server of the epresription service provider, a telecommunication network through with the prescriber's device communicates with the software and hardware of the service provider, another software application running at the pharmacy, and another communication network between the eprescription service provider's server and the pharmacy.

The communication network for communication between the prescriber's device and the eprescription service provider's server and the network for communications between the pharmacy's device and the eprescription service provider's server may be different networks or may be the same network, such as the internet.

While eprescription system of the present invention may utilize proprietary software at each of the aforementioned nodes, it is also possible to design a system that interfaces with either the pharmacist's or prescriber's device that requires the pharmacist or prescriber to have only general-purpose software, such as a standard web browser.

Innovative aspects of the eprescription system of the present invention include (1) real-time delivery of information to the prescriber at the time of preparing the prescription, when the patient is likely to be present with the prescriber and can answer any questions that may arise or be subject to further examination and (2) delivery of information to the prescriber that is customized based on information about the prescriber, information about the patient, and/or general information such as current weather, local pollen counts and other allergen data, etc. One advantage of the system is that it provides information to the prescriber prior to completion of the prescription so that the prescriber may tailor or change the prescription based on the delivered information. The information delivered to the prescriber (hereinafter sometimes referred to as the "message" for ease of reference and to distinguish from other data being exchanged between various nodes in accordance with the system) may comprise or include advertising or educational information. For instance, when a prescriber has chosen to prescribe a specific drug, the system has the capability to offer an alternative drug (possibly comprising a paid-for advertisement by a pharmaceutical company). The prescriber may then analyze the alternative drug and choose it instead, prior to completing the prescription. As another example, when a provider chooses a drug, the system may compare the chosen drug to the patients' active drug history, the DUR (Drug Utilization Review), to determine whether the chosen drug will result in an indication or contraindication. If so, the system may generate a message that alerts the provider to a potential indication/contraindication by the use of an "X" or "!" icon, depending on the severity of the interaction, and offer alternative drug(s) to the provider.

The system is very flexible and can be configured to deliver messages taking into account many different factors in addition to the patient and physician personal data. For instance, the system may be configured to transmit messages to any given prescriber only at predetermined intervals, such as one message for every two eprescriptions prepared.

The message can have an influence on the prescriber's prescription that is useful or beneficial to the patient and/or the prescriber in addition to being beneficial to the advertising entity (e.g., a pharmaceutical company).

Furthermore, since some of the messages delivered to the prescriber via the eprescription service may comprise advertising, the system also provides mechanisms for tracking the efficacy of such advertising and generating and delivering reports to the advertisers disclosing the efficacy of the advertising. Such usefulness of such functionality, of course, is not limited to advertising insofar as such efficacy data also may be useful in connection with the delivery of non-advertising information, such as warnings, recalls, contraindications, food and drug allergies, etc.

Through the use of appropriate APIs (Application Program Interfaces), the eprescription system of the present invention is adapted to interact with various third party software systems from which it can obtain relevant patient, prescriber, or other information, including, but not limited to various different commonly available EMR systems, EHR systems, and practice management software systems containing relevant information about the prescribers and the patients.

Relevant data points upon which the specific content of the messages to be delivered to the prescriber in connection with any given prescription may include, but is not limited to, information about the prescriber, such as location, age, gender, past prescribing habits, medical specialty, practice size, geographic location, socio-economic data about the geographic location of the prescriber's practice, decile, schooling, years in practice, etc. Information about the patient may include, for example, age, gender, height, weight, ethnicity, family medical history, patient prescription history, allergies, pre-existing medical conditions, insurance information (e.g., co-pay amount), educational level, home location, previous medical history, socio-economic data, etc. The information about the prescriber and/or patient may be sourced from any or all of the prescriber's own practice management system records, the practice management systems of other prescribers who are subscribers to the eprescription service and who treat the same patient, and third-party sources, such as public records or purchased information. The data also may include information not specific to the prescriber or patient per se, such as local or national laws, current local weather, local pollen counts and other allergen data, etc.

In one embodiment, the system handles up to 150 different data points, e.g., age, gender, etc. However the number of data points and the number of potential values for each data point (e.g., age=1, 2, 3, 4, 5, 6-10, 11-15, 16-20, 21-30, 31-40) is virtually limitless.

The eprescription service provider may download copies of the data point information from external sources and maintain the data its own database of prescribers, patients, and other data collected from the various sources. In other embodiments, the eprescription service provider may not store its own copy of some or all of the data, but rather access it remotely from the prescribers' practice management system or any other source in real time at the time it is needed (i.e., after a prescriber has begun creating a prescription). The eprescription service provider also may choose to store some data point information locally while accessing other data point information remotely in real time. The message delivered to the prescriber is delivered to the prescriber's device in any reasonable form, such as a banner appearing in a frame of the display adjacent a data entry frame in which the prescriber is entering the patient and prescription information. Alternately, it may be presented in a banner that consumes the entire screen of the prescriber's device and must be clicked through before the prescriber can return to the data entry screen to complete the prescription. The message may comprise or include text, graphics, video, audio, multi-media, or any other form of content capable of being delivered electronically. The message may contain an interface, such as a hyperlink to additional sources of information, such as regulatory web pages, pharmaceutical company web pages containing additional information about an advertised drug, The present invention provides a useful service both to prescribers and their patients on the one hand as well as to companies or other entities wishing to place information in front of prescribers or patients, such as pharmaceutical companies or government regulatory agencies. For instance, the messages may include advertisements concerning alternative drugs to the one being considered by the prescriber for prescription, available generic alternatives to name-brand drugs, a suitable alternative medicine based on Formulary data, coupons for discounts on the medicine being prescribed or an alternative medicine, a recall notice, a health warning, or a recommend medication(s) based on current disease state. For example, if a patient is on Lipitor and the system detects that the prescriber has noted that the patient has high triglycerides, the message may recommend that the prescriber add a drug, Trilipix that was developed to reduce triglycerides.

In accordance with further aspects of the invention, the eprescription system also may deliver information and advertisements to the patient in addition to the prescriber. For instance, the information available from the prescriber's practice management system database may include patients' e mail addresses. Hence, the eprescription service provider may e mail information, advertising, coupons, etc. to the patient's e mail address. The messages sent to patients also may be customized to the patient using the same or similar types of criteria as discussed above in connection with the customization of the messages sent to the prescribers.

Any messaging should be tailored to comply with the relevant laws and regulations of the pertinent countries, such as the HIPPAA medical privacy laws of the United States. For example, in the United States, an eprescription service should provide the option for any patient to opt out of receiving any advertising delivery. Some of the data points, for instance, may be whether the patient is covered by Medicare or Medicaid, in which case the patient is not allowed to receive coupons. Other data points an be used to comply with local laws and regulations, such as excluding the transmission of coupons to under age patients or exclude certain advertising in states such as Massachusetts and California that do not allow certain advertising to physicians. Furthermore, at least within the Untied States, all advertising messages should comply with FDA guidelines, such as including any required regulatory statements. For example, all brand-name drugs that are advertised will include their respective digital FDA-required fair balanced statements that spell out relevant drugs indications, contraindications, allergies, etc.

As noted above, the messages delivered to the prescribers (and/or patients) are customized based on various forms of information about the patient, prescriber, and/or other factors. The conditions for delivering any particular message to any particular prescriber during the prescription creation process (or any particular message to any particular patient) are dictated by a set of rules managed by the eprescription software. For instance, a pharmaceutical company may contract with an eprescription service provider to present a banner advertisement for Lipitor™ to (1) any cardiologist (2) in zip code 10001 (3) who is prescribing Crestor™ for a patient (each number in this sentence corresponding to a condition for presenting the particular advertisement). As another rule example, an advertiser may purchase the right to send a message containing a coupon for Nasonex™ to (1) any prescriber that is prescribing any allergy nasal spray to any patient (2) who either (a) has no insurance policy or (b) whose insurance policy provides for a co-pay of greater than $20 for Nasonex™.

In a typical eprescription system, the prescriber must click through a plurality of graphical user interfaces (GUIs) or screens in order to complete the prescription. For instance, a first GUI may require the input of the patient information and prescriber information (although, frequently, the prescriber information is automatically entered when the prescriber is using a registered computer or other device). A second GUI may require the input of the medication information, such as medicine, dosage, number of refills, etc. Additional GUIs provide interfaces for entering further information. Some GUIs may be optional, such as an option to be taken to an interface, such as an educational web page showing various potential alternate treatments, drugs, formularies, etc. to the one entered by the prescriber.

The message(s) in accordance with the present invention can be sent for display on the prescriber's monitor in between any of the data entry or other GUIs and/or in a frame or portion of any of the GUIs. For instance, a customized message based on the identity of the patient and prescriber can be generated after the prescriber enters the patient and prescriber data in the first GUI and the message is transmitted to the eprescription service provider and then presented within the next GUI (e.g., the GUI for entering the medication information) or before the next GUI is displayed. One or more separate messages may be sent over the course of the eprescription creation process. Messages may be displayed for a predetermined period before the next data entry GUI appears. Alternately, the message may require the prescriber to click on a "NEXT" button within the GUI to proceed to the next screen. A plurality of different messages may be presented sequentially at predetermined intervals during the electronic prescribing process. For instance, a side frame within a particular screen may contain an advertisement that changes every 15 seconds. The few above mentioned manners of presenting the messages are merely exemplary as the potential ways in which the messages can be presented to the prescribing physician are virtually limitless.

The eprescription system of the present invention delivers customized advertising and information dynamically using high-level logic rules and decision making capabilities. The logical rules for determining what messages to deliver to what prescribers (or patients) need not be based on absolute conditions, but may be based on a weighted evaluation of multiple factors.

Figure 1:
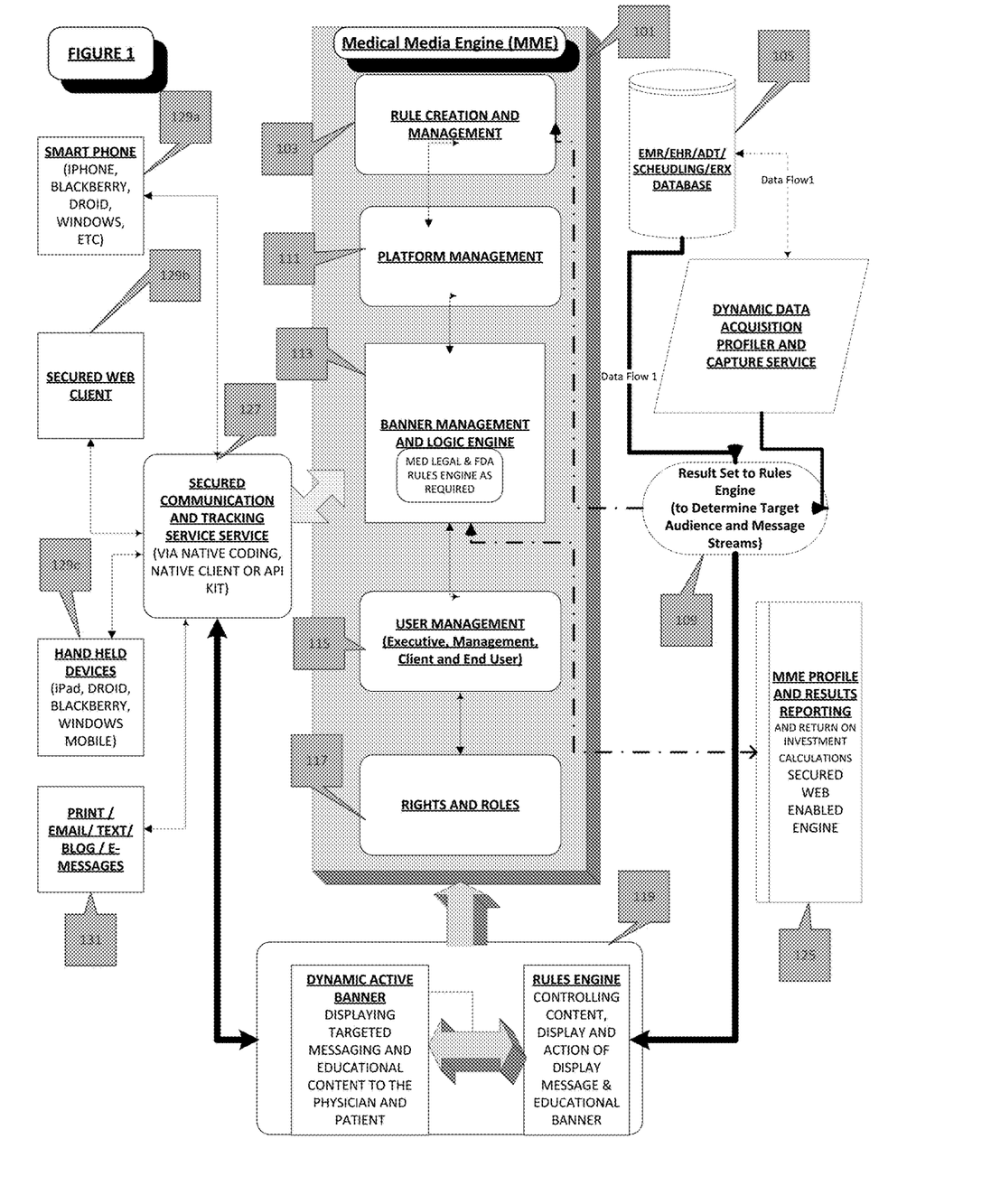
FIG. 1 is a functional block diagram of the various components involved in the practice of the invention according to one embodiment.

FIG. 1 is a block diagram illustrating the functional components involved in the pushing of messages to prescribers and/or patients in accordance with one particular embodiment of the present invention. The blocks do not necessarily correspond to distinct physical components, but rather to distinct functional concepts and basically represent software modules that can run on any reasonable platform, including computers, microprocessors, processors, digital signal processors. For instance, most of the software shown in FIG. 1 other than the prescribers' devices 129a, 129b, 129c can be running on a single server. Conceivably, some or all of the functionality described herein may be provided by or in combination with other forms of circuitry, including, but not limited to, state machines, combinational logic circuits, FPGAs, digital circuits, Application Specific Integrated Circuits (ASICs), analog circuits, processors, microprocessors, digital signal processors (DSPs), computers, software running on any of the above, and/or any combinations of the above (hereinafter "digital processing apparatus").

The invention is adapted to interface with a variety of different software applications and platforms and hardware platforms from which it may obtain the aforementioned prescriber, patient, and/or other information. These include various commercially available EMR systems, EHR systems, eprescription applications, patient management systems, etc. It also is designed to interface with a plurality of different platforms when sending messages to prescriber devices (or prescriptions to pharmacists). For instance, there are several different operating systems widely used by prescribers, pharmacists, and the general public for computers (e.g., Apple's Mac OS and Microsoft Windows) and smart phones (e.g., Google's Android operating system, Apple's IOS operating system, and Microsoft's Windows Mobile operating system). The ability to interface to different third-party operating systems and platforms is effected by the provision of a number of different APIs (application program interface), each adapted to translate data as needed between different platforms.

As shown in FIG. 1, the system comprises a number of functional modules or components. The core of the system is the Medical Media Engine (MME) 101, which comprises a Rule Creation and Management module 103, a Platform Management module, a Banner Management module, and a User Management module 115. The Rule Creation and Management module 103 provides two primary functions, namely, the creation/input of rules and the execution of those rules to deliver messages to prescribers (and/or patients). Thus, it is software that provides the necessary interfaces, such as graphical user interfaces, to permit automated or manual creation and entry of rules that dictate which messages are delivered to which prescribers under which conditions, as discussed above, e.g., (1) for cardiologists (2) in zip code 10001 (3) prescribing Lipitor™, deliver an advertisement for Crestor™.

The Rule Creation and Management Module 103 and Database 105 also can generate Result Sets 109 that disclose an affected audience of prescribers and/or patients for a prospective (or existing) rule so as to allow advertisers and other users of the system to determine the size and/or other characteristics of the potential audience for a message as dictated by the prospective rule. For example, a prospective rule to deliver an advertisement to all cardiologists in the 10001 zip code might generate a Result Set 109 indicating that these conditions correspond to a potential audience comprising 2000 prescribers and that those prescribers prescribe Lipitor™ on average 2.1 times a day and Crestor™ on average 1.8 times a day. This information is useful to advertisers, for instance, to help determine what rules to create. They also are useful to the eprescription service provider to assist in determining appropriate pricing for advertising in accordance with any specific rule.

The Rule Creation and Management module 103 also provides the functionality for executing the rules that have been input into the system. More specifically, when a prescriber enters prescription data into his or her device (e.g., a smart phone 129a, a secure Web client, 129b, a handheld device 129c) to start creation of a prescription, that data is transmitted via a Secured Communication and Tracking Service 127 to the MME 101. Before the prescriber is permitted to complete the prescription, the MME 101 will determine if the prescriber qualifies under any of the rules in effect for delivery of one or more particular messages to the prescriber, and, if so, will generate and send the prescriber such a message as described hereinabove. More specifically, the Secured Communication and Tracking Service 127 feeds platform information to a Platform Management module 111. The platform data usually can be determined from the format or other characteristics of the data received from the prescriber's device. The Platform Management module 111 determines the platform of the prescriber's device and determines which API or other interface mechanism to use to decipher the prescription information as well as which interface mechanism to use to send a message back to the prescriber's device.

If the prescriber does not qualify under any of the rules for targeted advertising, then the system may send him/her a general advertisement or educational message. Of course, the system also may send general advertisements and educational messages to prescribers who did qualify under the rules of one or more targeted advertisements or other messages in addition to the targeted advertisements.

The Platform Management module 111 deciphers the prescription information and forwards it to the Rule Creation and Management module 103, which parses the prescription data to extract the relevant data. Particularly, the prescription information received from the prescriber's device 120a, 129b or 129c usually will include at least the prescriber's identity and the patient's identity, and may also include the medication the prescriber intends to prescribe. It then queries the Eprescription Database 105, which stores the prescriber, patient, and other data as previously described, to generate a Result Set 109 describing the relevant data points as derived based on the specific information in the prescription.

The database 105 also may further interact with a Dynamic Data Acquisition Profiler and Capture Service 127 that dynamically accesses other data sources, such as third party data sources, to gather additional data that may be relevant to one or more of the rules. For instance, such sources may provide additional information about patients or prescribers, weather information, demographic information, daily allergen information, etc. Any such data is added to the Result Set 109.

The Rule Creation and Management Module 103 determines which, if any, rules match the Result Set 109 and then determines which message(s) should be returned to the prescriber in accordance therewith.

The Rule Creation and Management Module 103 generates a dataset disclosing what message(s) are to be sent to the prescriber's device and forwards the dataset to the Platform Management Module 111. The Platform Management Module 111 interfaces with the Banner Management module 113 to collectively assemble the precise content to be delivered within the message. Particularly, not only does the message need to be formatted according to the platform of the prescriber's device, but the actual substantive content of the message may differ depending on the platform of the prescriber's device. For instance, there is much less screen space on a typical smart phone than on a typical laptop or desktop computer. Also, the speed at which data can be downloaded to a wireless device communicating with the MME through a 3G wireless connection may be much slower than it is for a desktop computer hardwired to an internet connection. Accordingly, for instance, a particular paid for advertisement message that is to be sent to a smart phone may be presented in the form of one or more click-through screens that occupy the entire screen of the handheld device, whereas, if the message is being delivered to a laptop computer, the message may be presented in a side frame on the screen while most of the screen continues to display the main data entry screen to the prescriber. In other cases, the smart phone message may simply contain less text or graphics that the message intended for a desktop computer.

In any event, the Banner Management and Logic Engine 113 selects the appropriate content of the message and the Platform Management module 111 converts it to the proper format for the platform of the prescriber's particular device 120a-129c.

The Secured Communication and Tracking Service 127 then sends the message to the prescriber's device 129a-129c.

Messaging to a patient's device 131 e.g., an e mail to the patient's e mail address) follows largely the same pattern with the differences in specific operations being largely obvious based on the different circumstances. For instance, unlike messages sent to the prescriber (who is in the middle of the process of preparing a prescription in real time), messages sent to patients need not be sent out in real time, but may be delayed for any desired amount of time.

Once the message has been delivered, the prescriber can then complete the electronic prescription and the eprescription service can forward the prescription to the proper pharmacy largely in accordance with conventional eprescription system operations (not necessarily illustrated in FIG. 1).

The system also provides additional functionality. For instance, a User Management Module 115 in MME 101 manages interaction with the system by administrators and other functional users of the eprescription system 100, e.g., employees of the eprescription service provider as well as the entities that use the service to place advertisements or other message content in front of patients and prescribers. Such functions may include controlling access to the various different aspects of the system as a function of the particular user's clearance level. For instance, an administrator may have access to all data and functions in the system, whereas an advertiser may be granted access only to information relevant to itself. The User Management function 115 interfaces with a Rights and Roles Database 117, which includes the identities of the authorized users of the system and any rights and restrictions applicable to them.

The aforementioned Result Sets 109 also are sent to a Data Collection module 119. Data Collection Module 119 also interfaces with the Secured Communication and Tracking Service 127 to collect data as to how the prescribers and patients act responsive to the messages (e.g., how many and which patients opted out of the message service, how many click-throughs a prescriber or patient proceeded through, whether the patient or prescriber printed anything, whether the patient read an e mail, etc.; hereinafter "response data"). Specifically, Data Collection Module 119 collects and correlates information from the Result Sets 109 with the patient and prescriber response data. The Data Collection module 119 can then be queried to derive information about the effectiveness of the advertising and other messaging.

Specifically, the Banner Management and Logic Engine 113 includes further functionality to query the Data Collection Module 119 and generate various reports 125 that may be useful to the epresription service provider, advertisers, and other entities that use the system to push messages to prescribers and/or patients. The types of reports that may be generated are virtually limitless. Merely a couple of examples are reports indicating the number of times a specific advertisement has been delivered and to whom (e.g., either specific identities or demographically) or the percentage of prescribers that received the advertisement that prescribed a particular drug versus the percentage of prescribers who were not shown that advertisement that prescribed that drug.

This information can be used by the eprescription service provider as well as advertisers and other entities to determine the efficacy of the advertising/messaging and for purposes of invoicing, e.g., in situations where charges are invoiced on a per-view basis.

Figure 2:
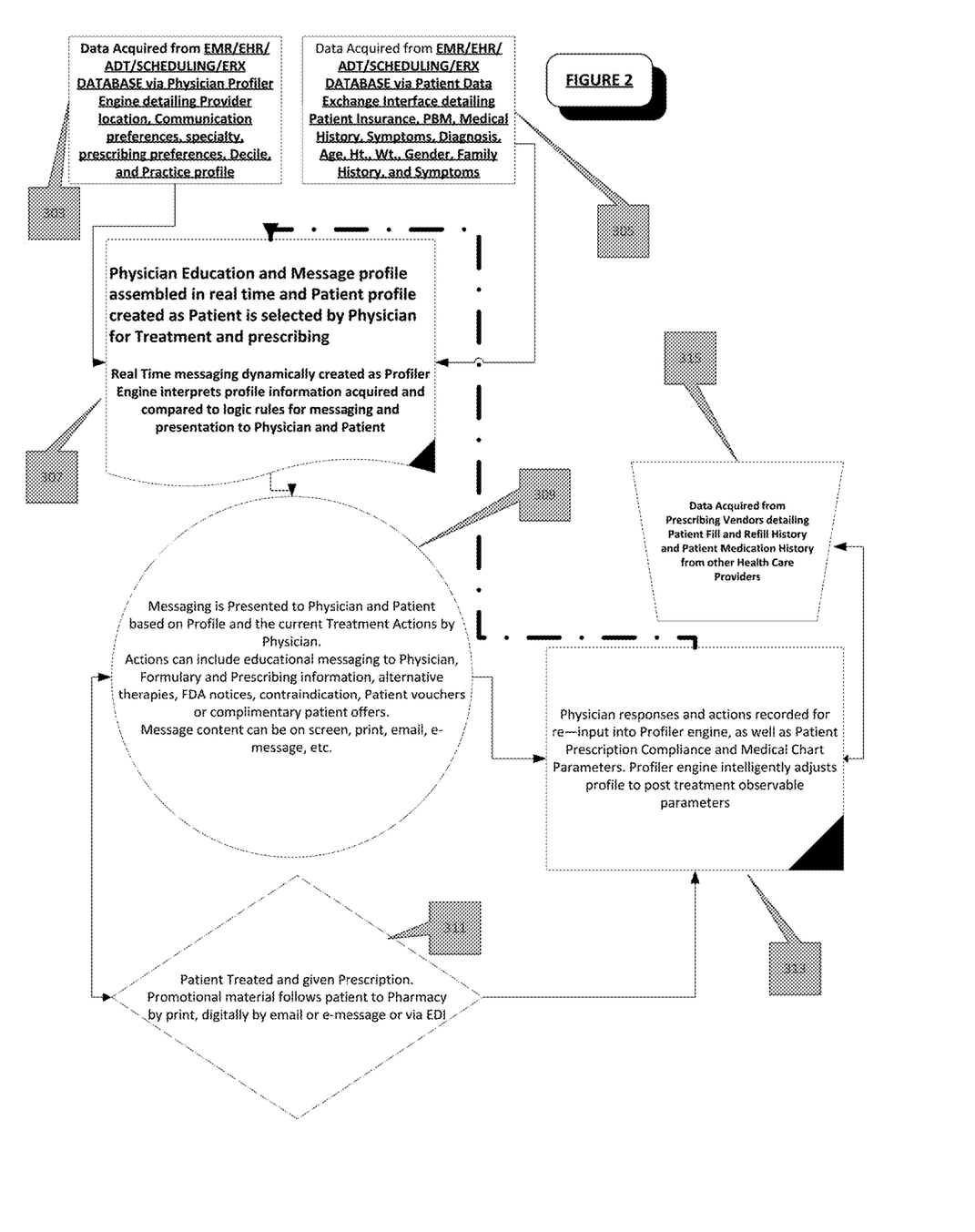
FIG. 2 is a flow chart illustrating operation in accordance with one embodiment of the invention.

FIG. 2 is a simplified flowchart illustrating data flow in accordance with one exemplary embodiment of the invention. This flowchart illustrated flow commencing (at steps 303 and 305) after the MME 101 has received the initial prescription information (prescriber identity, patient identity, and usually medicine) from the prescriber's device. In step 303, the information about the prescriber is gathered from the various aforementioned sources, including, but not limited to, the eprescription database (e.g., 109 in FIG. 1), the prescriber's practice management systems, such as EMR, EHR, ADT (Admission, Discharge and Testing), and ERX (Electronic Prescribing) databases as well of other subscribers to the eprescription service. Likewise, information about the patient is gathered in step 305 from some of the same sources and/or additional sources. In step 307, the prescriber and patient profiles are assembled and a suitable message is selected for transmission to the prescriber before he/she completes the prescription. Next, in step 309, the message is presented to the prescriber and/or patient. As previously noted, the message may include information such as educational information, formulary and prescribing information, alternative therapies, FDA notices, contraindications, coupons, offers, and advertising.

In step 311, the prescriber completes the prescription. Additional messages may be sent to the patient via e mail and/or to the filling pharmacy. In step 313, data for updating the eprescription service provider's database is assembled and entered into the database. Such information may include, but is not limited to, whether the patient filled the prescription at the pharmacy, how the prescriber responded to the message(s), whether and how the patient responded to any e mails or other messages sent to him/her, and patient data entered into the prescriber's or other physicians' practice management systems (step 315) after the prescription was filled (and which might be indicative of the efficacy of the prescribed medication).

Figure 3:
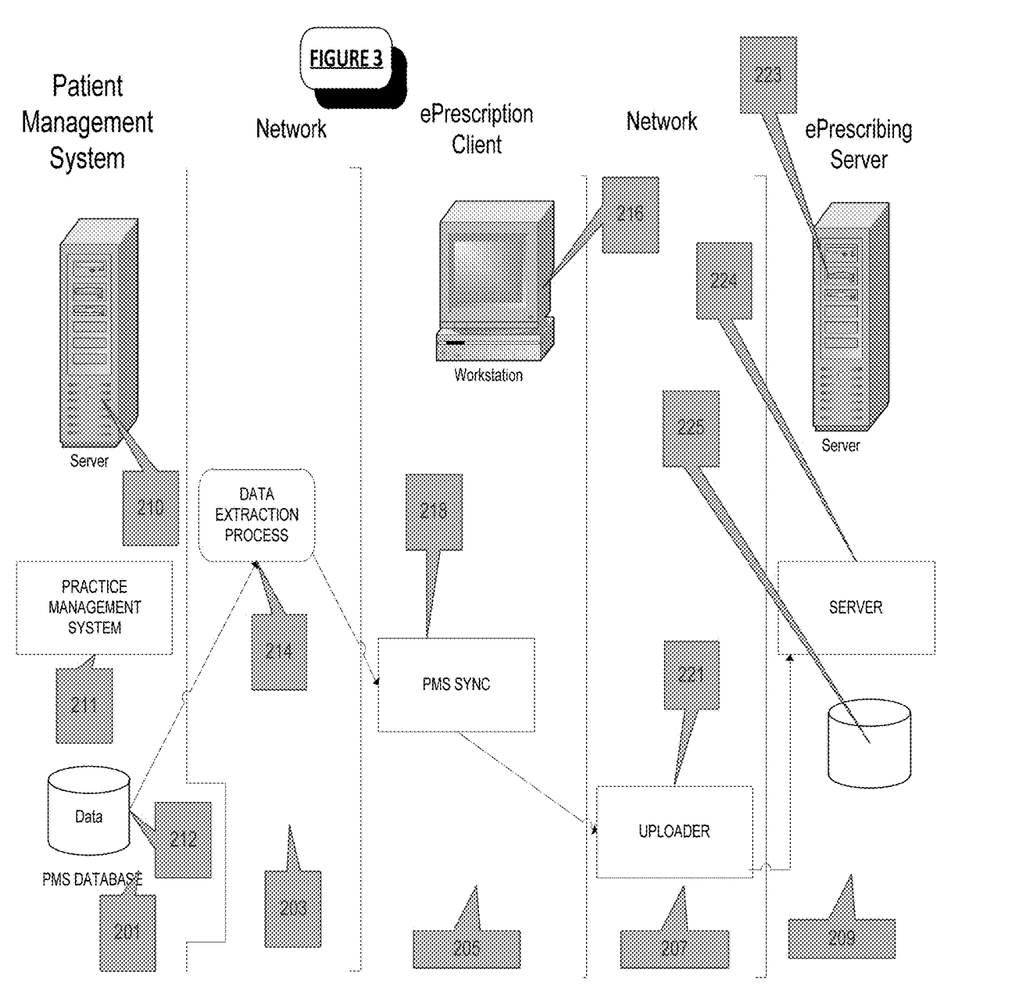
FIG. 3 is a flow diagram illustrating interaction of the various software and hardware components in accordance with one embodiment of the invention.

FIG. 3 is a flow diagram illustrating the layers involved in the extraction and storage of data from the prescriber's practice management system and the components involved therein. The different columns 201, 203, 205, 207, 209 correspond to the different conceptual layers of the overall system.

The first layer on the left of the diagram is the prescriber's practice management software 211 and hardware 210. The prescriber's practice management software commonly is under the possession, control, or custody of the prescriber or at a collocation site from which the prescriber leases hardware and/or software. This layer comprises, for instance, a physical server 210 running the prescriber's practice management system 211 and maintaining a database 212 of the prescriber's patients' medical and personal data. The database 212 also commonly will contain information about the prescriber and his/her practice.

At the other end of the spectrum is the eprescription back end layer 209. This layer comprises virtually all of the software shown in FIG. 1 other than the prescriber devices 129a-129c and patient devices 131. Physically, there one or more servers 223 running the server software 224 as primarily described above in connection with FIG. 1.

Column 205 corresponds to the eprescription client software layer, which comprises the software that runs on the prescriber's device(s) 216, which corresponds to any of devices 129a-129c in FIG. 1. The eprescription client module 205 serves two primary functions. First, it interfaces with the eprescription system at the time of creating eprescriptions largely as described above in connection with FIG. 1. Secondly, it includes a practice management system synchronization module 218 that is an intermediary between the prescriber's practice management system 211 and the eprescription service provider's system 209 to upload the patient and prescriber data from the practice management system database 212, typically via a network layer 203, and forward it to the eprescription service provider's facility 209 for storage in the eprescription database 225, typically via another network layer 207.

In operation, when a prescriber subscribes to the eprescription service, the eprescription client software is loaded on the prescriber's device(s). It includes a PMS synchronization module 218 that performs a data extraction process 214 that interfaces with the practice management system 211 and database 212 to retrieve the patient and prescriber data via a network 203. Thereafter, the PMS synchronization module 218 sends that data to the eprescription service provider's server 224 via another network connection 207 for storage in the database 225 (which corresponds to database as Database 109 of FIG. 1) for storage.

Having thus described a few particular embodiments of the invention, various alterations, modifications, and improvements will readily occur to those skilled in the art. Such alterations, modifications, and improvements as are made obvious by this disclosure are intended to be part of this description though not expressly stated herein, and are intended to be within the spirit and scope of the invention. Accordingly, the foregoing description is by way of example only, and not limiting. The invention is limited only as defined in the following claims and equivalents thereto.

The invention claimed is:

1. A method of interfacing with an electronic prescription system to transmit a customized message to a prescriber device responsive to entry of prescription information for one patient of a plurality of patients into said electronic prescription system from said prescriber device, said prescriber device having a display, the method comprising:
receiving from said electronic prescription system electronic prescription information pertaining to a prescription for one patient of a plurality of patients, the electronic prescription information including at least patient identity, prescriber identity, and medication being prescribed;
accessing a database using at least the patient identity to obtain patient information;
accessing a database using at least the prescriber identity to obtain prescriber information, including at least past prescribing habits;
accessing a database using at least the medication being prescribed, the patient identity, and the prescriber identity including past prescribing habits to obtain medication information;
prior to the prescriber completing the prescription for the medication being prescribed, automatically generating a message containing the medical information, and transmitting the message to said electronic prescription system for display on said display;
receiving information modifying the prescription from the prescriber following the display of the message; and
generating a modified prescription responsive to the information modifying the prescription.

2. The method of claim 1 further comprising: maintaining an electronic database of personal information about a plurality of physicians and a plurality of patients.

3. The method of claim 1, wherein the accessing comprises querying the electronic database.

4. The method of claim 1 wherein the message comprises an advertisement.

5. The method of claim 1 wherein the message comprises educational content about a medication being prescribed.

6. The method of claim 1 wherein the personal information comprises up to 150 different data points.

7. The method of claim 6, wherein said data points comprise a plurality of the following: prescriber location, prescriber age, prescriber gender, prescriber past prescribing habits, the prescriber's medical specialty, prescriber practice size, socio-economic data about the geographic location of the prescriber's practice, prescriber decile, the prescriber's educational background, prescriber years in practice, patient age, patient gender, patient height, patient weight, patient ethnicity, patient family medical history, patient prescription history, patient allergies, patient pre-existing medical conditions, patient insurance information, patient educational level, patient home location, patient previous medical history, and patient socio-economic data.

8. The method of claim 1, further comprising:
collecting the patient personal information and prescriber personal information from a practice management system of the prescriber.

9. The method of claim 1, wherein the patient personal information comprises data collected from the prescriber and data collected from other prescribers.

10. The method of claim 1, wherein automatically generating a message comprises selecting message content from a store of messages.

11. The method of claim 1, further comprising:
selecting a second message to be transmitted to the patient as a function of the personal information; and
transmitting the second particular message to the patient.

12. A system of interfacing with an electronic prescription system to transmit a customized message to a prescriber device responsive to entry of prescription information for one patient of a plurality of patients into said electronic prescription system from said prescriber device, said prescriber device having a display, the system comprising:
a processor; and
memory operatively connected to the processor and configured to cause the processor to execute the following steps:
receive from said electronic prescription system electronic prescription information pertaining to a prescription for one patient of a plurality of patients, the electronic prescription information including at least patient identity, prescriber identity, and medication being prescribed;
access a database using at least the patient identity to obtain patient information;
access a database using at least the prescriber identity to obtain prescriber information, including at least past prescribing habits;
access a database using at least the medication being prescribed, the patient identity, and the prescriber identity including past prescribing habits to obtain medication information;
prior to the prescriber completing the prescription for the medication being prescribed, automatically generate a message containing the medical information, and transmit the message to said electronic prescription system for display on said display;

receive information modifying the prescription from the prescriber following the display of the message; and generate a modified prescription responsive to the information modifying the prescription.

13. The system of claim 12, wherein said memory is further configured to cause the processor to execute the following step: maintain an electronic database of personal information about a plurality of physicians and a plurality of patients.

14. The system of claim 12, wherein the accessing comprises querying the electronic database.

15. The system of claim 12, wherein the message comprises an advertisement.

16. The system of claim 12, wherein the message comprises educational content about a medication being prescribed.

17. The system of claim 12, wherein the personal information comprises up to 150 different data points.

18. The system of claim 17, wherein said data points comprise a plurality of the following: prescriber location, prescriber age, prescriber gender, prescriber past prescribing habits, the prescriber's medical specialty, prescriber practice size, socio-economic data about the geographic location of the prescriber's practice, prescriber decile, the prescriber's educational background, prescriber years in practice, patient age, patient gender, patient height, patient weight, patient ethnicity, patient family medical history, patient prescription history, patient allergies, patient pre-existing medical conditions, patient insurance information, patient educational level, patient home location, patient previous medical history, and patient socio-economic data.

19. The system of claim 12, wherein said memory is further configured to cause the processor to execute the following step: collecting the patient personal information and prescriber personal information from a practice management system of the prescriber.

20. The system of claim 12, wherein the patient personal information comprises data collected from the prescriber and data collected from other prescribers.

21. The system of claim 12, wherein automatically generating a message comprises selecting message content from a store of messages.

22. The system of claim 12, wherein said memory is further configured to cause the processor to execute the following step: select a second message to be transmitted to the patient as a function of the personal information; and transmit the second particular message to the patient.

* * * * *